US00PP35914P2

(12) United States Plant Patent
Contreras

(10) Patent No.: US PP35,914 P2
(45) Date of Patent: Jul. 2, 2024

(54) ***PHILADELPHUS* PLANT NAMED 'ORSTPHILX1'**

(50) Latin Name: ***Philadelphus* hybrid *(Philadelphus coronarius 'Icezam'* x *Philadelphus lewisii* 'Blizzard'**
Varietal Denomination: ORSTPHILx1

(71) Applicant: Oregon State University, Corvallis, OR (US)

(72) Inventor: Ryan N. Contreras, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 18/214,040

(22) Filed: Jun. 26, 2023

(51) Int. Cl.
*A01H 5/02* (2018.01)
*A01H 6/48* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP25,565 P2 * 5/2015 Zampini ..... A01H 5/02 Plt./226

* cited by examiner

*Primary Examiner* — Karen M Redden
(74) *Attorney, Agent, or Firm* — Klarquist Sparkman, LLP

(57) ABSTRACT

A new *Philadelphus* variety distinguished by its upright and vigorous, yet compact growth habit, dense branching, deep green foliage late into the season, and prolific flower production.

4 Drawing Sheets

Latin name of the genus and species of the plant claimed: *Philadelphus* hybrid (*Philadelphus coronarius* 'Icezam'× *Philadelphus lewisii* 'Blizzard').

Variety denomination: 'ORSTPHILx1'.

BACKGROUND

The present application relates to a new and distinct variety of *Philadelphus* named 'ORSTPHILx1'. 'ORSTPHILx1' is an interspecific hybrid resulting from a controlled cross between *Philadelphus coronarius* 'Icezam' (patented; U.S. Plant Pat. No. 25,565) as the seed parent x *Philadelphus lewisii* 'Blizzard' (unpatented) as the pollen parent. The cross was made and seedling grown in Corvallis, Oregon. The original accession was designated H2013-006-012. The seedling was field planted in 2015 and then transplanted to its current location in 2017. 'ORSTPHILx1' differs from its seed parent most obviously by lacking variegation that is present in 'Icezam'. Most apparent difference between 'ORSTPHILx1' and its pollen parent, 'Blizzard', is its improved branching in container production. Light pruning leads to compact, well-branched, and dense shrubs of 'ORSTPHILx1', whereas 'Blizzard' presents few branches and requires more management to develop a quality container plant. Fruit of 'Blizzard' (1 cm) are larger than 'ORSTPHILx1' (0.7 cm).

SUMMARY

Plants of the new *Philadelphus* have not been observed under all possible combinations of environmental conditions and cultural practices. However, the following traits have been consistently observed, and are a unique combination of characteristics for 'ORSTPHILx1':

1. Upright and vigorous, yet compact growth habit
2. Dense branching
3. Deep green foliage late into the season
4. Highly floriferous Asexual reproduction of this new variety by vegetative cuttings shows that the foregoing characteristics come true to form, are firmly fixed, and are established and transmitted through succeeding propagations.

Certain characteristics of this variety may change with changing environmental conditions (such as photoperiod, temperature, moisture, soil conditions, nutrient availability, or other factors). Thus, the phenotype may vary somewhat with variations in environmental conditions without any variance in genotype. Color descriptions and other terminology are used in accordance with their ordinary dictionary descriptions, unless the context clearly indicates otherwise. Color designations (hue/value/chroma) are made with reference to The *Royal Horticultural Society Colour Chart* (R.H.S.) $6^{th}$ edition, 2015.

Figure 1:
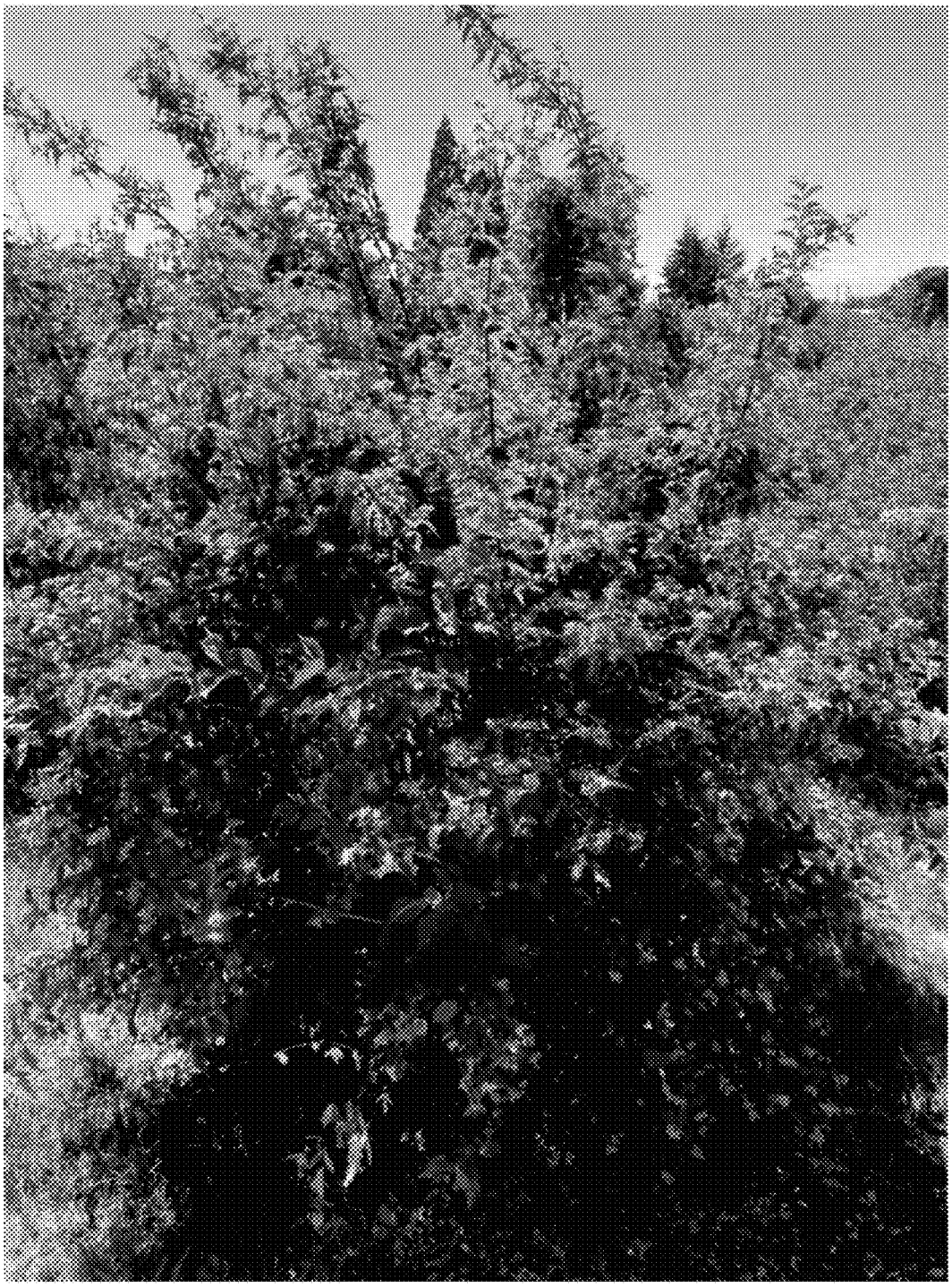
FIG. 1 is a photograph showing a side perspective of the original plant that was field planted in 2015 and left unpruned. The photo was taken on Jun. 22, 2021.
Figure 2:
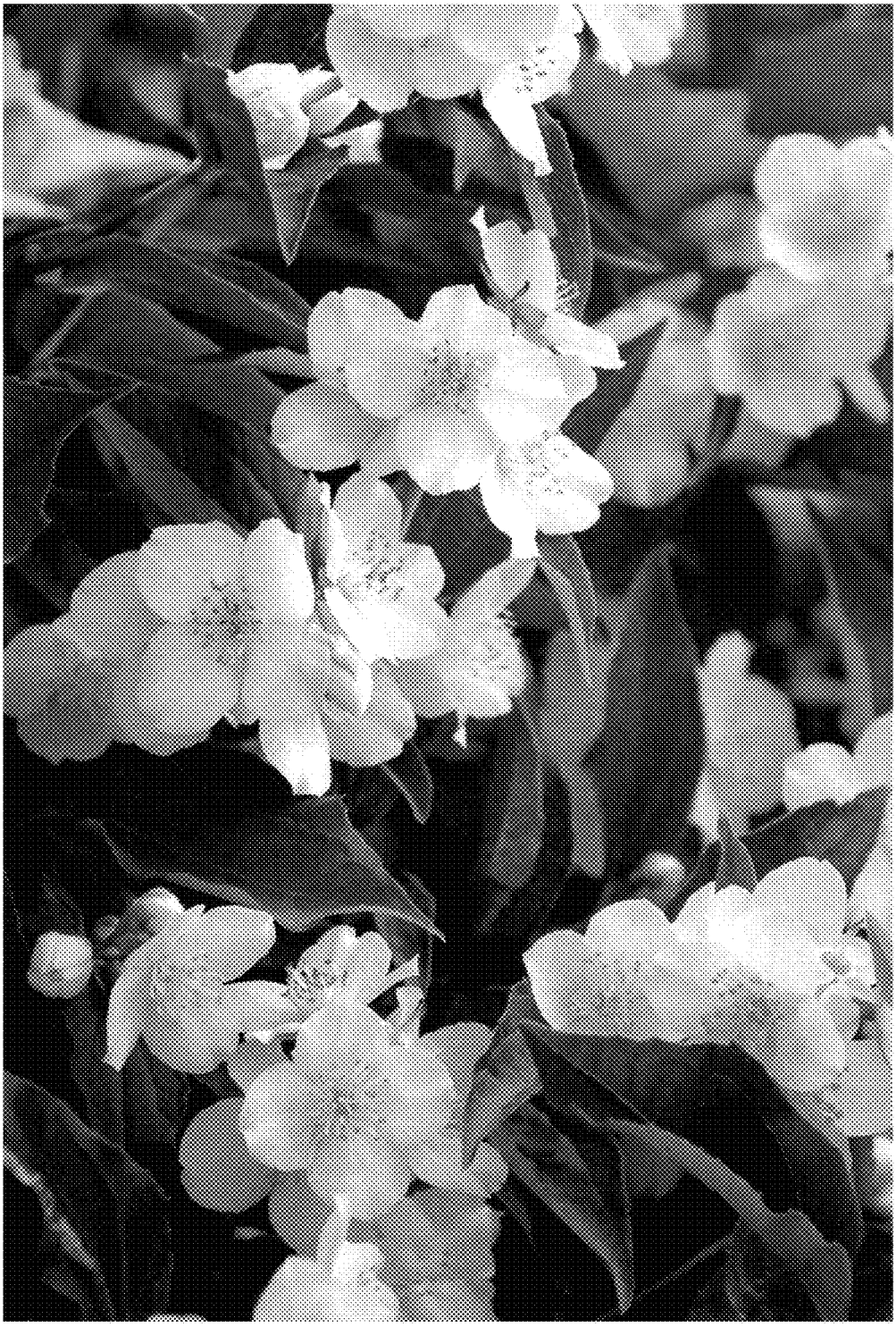
FIG. 2 is a photograph showing a close-up of the flowers. The photo was taken on Jun. 3, 2021.
Figure 3:
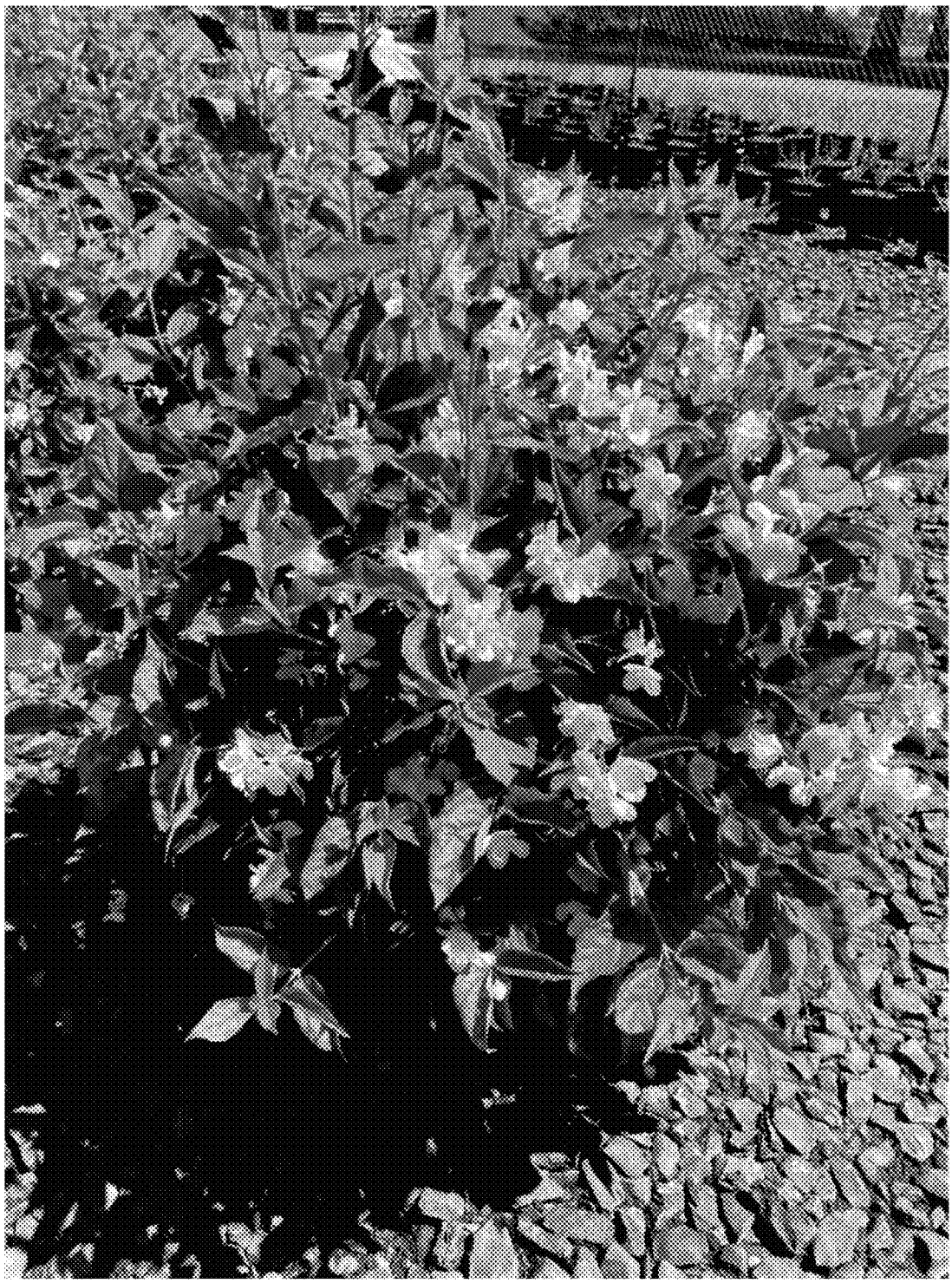
FIG. 3 is a photograph of a plant in container production evaluation. The photo was taken on Jun. 3, 2021.
Figure 4:
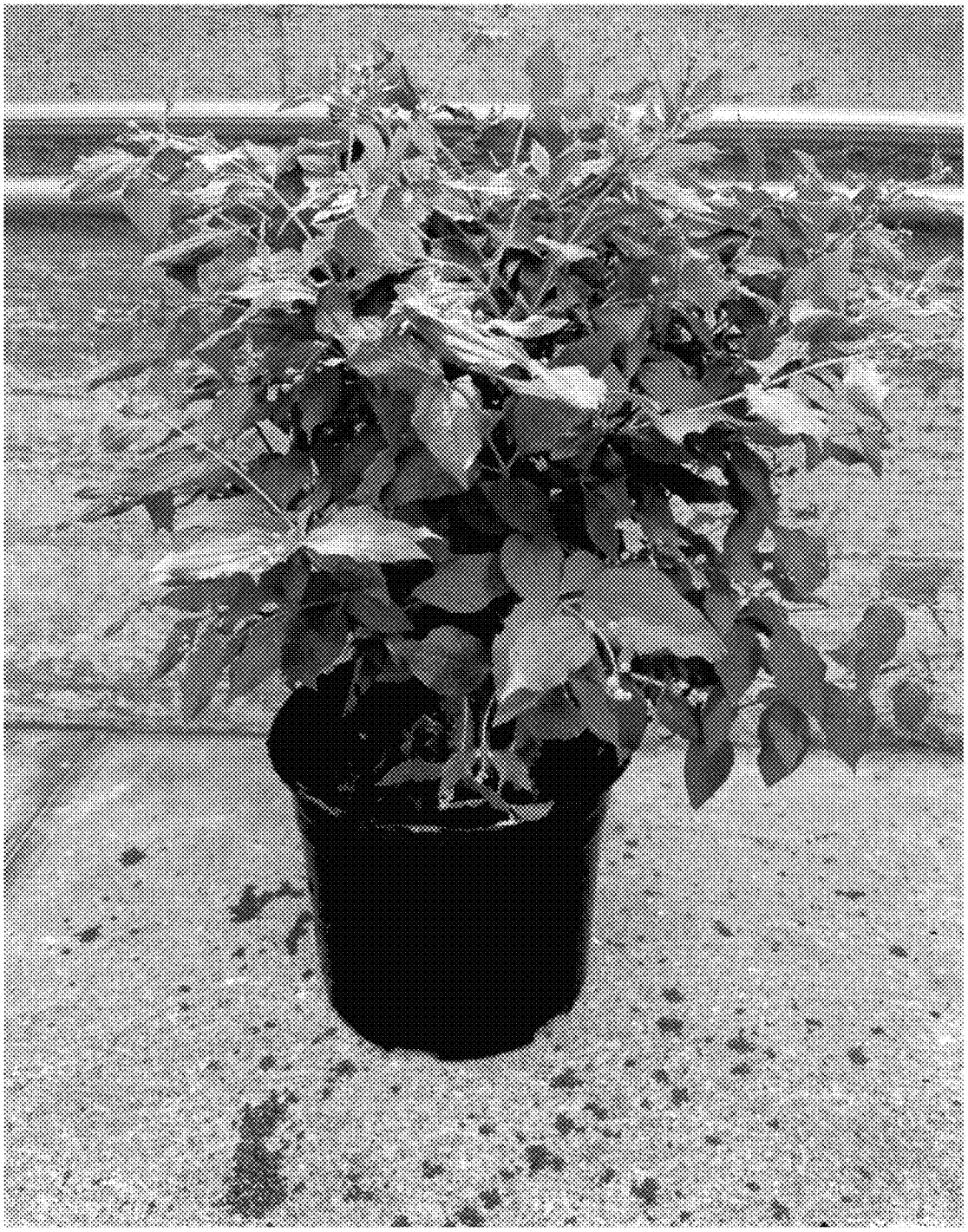
FIG. 4 is a photograph of a container plant in a greenhouse. The photo was taken on Mar. 11, 2023.

The color photographs show typical specimens of the new variety and depict the color as nearly true as is reasonably possible to make the same in a color illustration of this character. It should be noted that colors may vary, for example due to lighting conditions at the time the photograph is taken. Therefore, color characteristics of this new variety should be determined with reference to the observations described herein, rather than from the photograph alone.

DETAILED BOTANICAL DESCRIPTION

The following is a detailed description while observing mature plants propagated from stem cuttings. Such plants ranged between two and five years of age and were found to have consistent morphology, apart from size (younger plants are smaller). Plants were propagated in protected environments, then grown outdoors in partial shade in Corvallis, Oregon, USA. Flowering data was collected during March 2023 on plants that were induced to flower in a glasshouse.

A container plant that was 2-3 years from cutting was used to describe all traits except mature size, which was measured from original seedling that was unpruned and 6-7 years old when evaluated at the end of the 2022 growing season. The plant was field planted on Apr. 29, 2015, and transplanted to its final location on Oct. 9, 2017.

Parentage:

*Seed parent.*—*Philadelphus coronarius* 'Icezam'.

*Pollen parent.*—*Philadelphus lewisii* 'Blizzard'.

Plant:

*Type.*—Deciduous shrub.

*Growth habit.*—Compact, dense, upright.

*Height and spread.*—Mature height and width is approximately 175 cm×140 cm.

*Hardiness.*—Predicted to be USDA Zone 5 based on parentage.

*Growth rate.*—Moderate.

*Propagation.*—Stem cuttings root at approximately 85%.

Stem:

*Stem shape.*—Round.

*Stem color.*—New growth RHS 138B, current season RHS 183A, previous years RHS 199D, exfoliation color RHS 183A.

*Stem surface.*—Glabrous with stems exfoliating after 2-3 years in a blocky pattern.

*Internode length.*—3.7 cm to 5.9 cm with an average of 4.9 cm.

Leaves:

*Heterophylly size differences.*—Most leaves are smaller with nearly entire (ciliate) margins and others are larger with more prominent teeth.

*Leaf length.*—Average is 7 cm (including petiole), but can reach 10 cm.

*Leaf width.*—Average is 2.6 cm, but can reach 4.1 cm.

*Shape.*—Ovate.

*Apex.*—Narrowly acute, mucronate.

*Base.*—Obtuse with some leaves slightly oblique.

*Margin.*—Ciliate, most leaves sparsely and variably toothed, some more prominent.

*Leaf surface.*—Young foliage is glossy and glabrous; mature foliage adaxially mostly smooth, slightly undulate to sub-bullate, some leaves with sparse stellate pubescence giving slightly scabrous feel.

*Venation pattern.*—Pinnate, somewhat arcuate, pubescent abaxially.

*Leaf blade length.*—24.4 mm.

*Leaf blade color.*—New foliage is glossy with adaxial and abaxial surface color RHS 143A, progressing to intermediate foliage with adaxial and abaxial surface color RHS 141A, maturing to adaxial surface color RHS N134A and abaxial surface color RHS 137C.

*Leaf arrangement.*—Opposite, simple.

*Petiole.*—Color: RHS 141B. Length: Typically 7.5 mm, but can reach 9.5 mm. Texture: Grooved adaxially, sparsely pubescent.

Flowers:

*Inflorescence type.*—Raceme.

*Inflorescence.*—Racemes of 5 to 9 flowers with an average of 7.

*Inflorescence size.*—6.6 cm.

*Bud.*—Shape: Ovoid. Length: 13.2 mm after sepal separation; 10.6 mm prior to sepal separation. Diameter: 7 mm after sepal separation; 4.9 mm prior to sepal separation. Color: RHS 145B pre-sepal separation; RHS 149D after sepal separation.

*Individual flower.*—Shape: Rotate. Diameter: 3.6 cm. Depth: 1.9 cm. Aspect: Outward, some slightly downward. Persistence: Self-cleaning.

*Petals.*—Petals per Flower: 4. Arrangement: Cruciform. Shape: Broadly ovate to sub-orbicular. Color: RHS 155C upper and lower surfaces. Petal Margin: Entire. Texture: Abaxial is smooth; adaxial is smooth with fine venation. Length: 19.3 mm. Width: 14.8 mm.

*Stamen.*—Number: 20. Color: Filament: RHS NN155C. Anther: RHS 7A. Attachment: Basifixed. Pollen: Production heavy, color RHS 7A.

*Pistil.*—Number: 1 pistil with 3-4 fused styles and stigmas. Length: 8 mm. Style: Length: 6.6 mm. Color: RHS N155C. Stigma: Length: 1.3 mm. Shape: Flat. Color: RHS 4C. Ovary Color: RHS 4C.

*Pedicel.*—Length: 4.4 mm to 6.7 mm. Diameter: 0.5 mm. Texture: Slightly pubescent. Color: RHS 138B.

*Peduncle.*—Length: Peduncle is technically absent. The entire inflorescence is composed of rachis since the flowers are attached at the base of the stalk. From the base to the next node is 3.5 cm to 8 cm. Texture: Slightly pubescent. Color: RHS 138B.

*Sepals.*—Arrangement: Cruciform. Shape: Teardrop. Apex: Acute. Base: Truncate. Margin: Entire. Number: 4. Length: 5.3 mm. Width: 3.5 mm. Texture: Slightly pubescent. Color: 145B upper and lower surfaces.

*Date of bloom.*—Approximately May 8 to June 13.

*Lastingness of individual blooms.*—3-5 days.

*Flower fragrance.*—Complex mixture of citrus flowers and grape soda; fruity.

*Fruit.*—0.7 cm long×0.5 cm wide. Four-parted capsule. Begins at 154C in color, transitioning through variable colors including irregular marking that are N74A in color. After desiccating is 198C in color. Seeds are minute, nearly dust-like, and N199D in color.

Disease/pest resistance: No formal assertion is made regarding its resistance, but this plant has remained asymptomatic from bacterial blight caused by *Pseudomonas syringae*, despite growing in a location with frequently observed incidence of the disease on related seedlings and cultivars.

I claim:

1. A new and distinct variety of *Philadelphus* plant named 'ORSTPHILx1', substantially as illustrated and described herein.

* * * * *